United States Patent [19]
Semeria et al.

[11] Patent Number: 5,994,586
[45] Date of Patent: Nov. 30, 1999

[54] PROCESS FOR THE PREPARATION OF 2-AMINOALKANE-1,3,4-TRIOLS

[75] Inventors: Didier Semeria, Courtry; Bernadette Luppi, Sevran; Michel Philippe, Wissous, all of France

[73] Assignee: L'Oreal, Paris, France

[21] Appl. No.: 08/732,573

[22] Filed: Oct. 15, 1996

[30] Foreign Application Priority Data

Oct. 16, 1995 [FR] France ................................. 95 12099

[51] Int. Cl.$^6$ ................................................ C07C 215/00
[52] U.S. Cl. ......................... 564/506; 564/355; 564/503
[58] Field of Search ................................. 564/506, 355, 564/503

[56] References Cited

FOREIGN PATENT DOCUMENTS

| 500437 | 8/1992 | European Pat. Off. . |
|---|---|---|
| 646572 | 4/1995 | European Pat. Off. . |
| 887652 | 7/1953 | Germany . |

OTHER PUBLICATIONS

M. Viscontini, "Reduction des substances Beta–amino–alpha, gamma–dicarbonylees; une nouvelle synthese de l'allo–DL–phenyl–3–amino–2–propane–diol–1,3 (DL–erythro–phenylserinol)," *Helvetica Chimica Acta*, vol. XXXV, Oct. 1952, pp. 1803–1805.

March, "Reduction of Nitroso Compounds and Hydroxylamines to Amines," *Advanced Organic Chemistry*, 1985, John Wiley & Sons, 3d Ed., p. 1105.

Houben–Weyl, "Reduktion von Oximen (Isonitros overbindungen) und Hyroxylaminen," *Methoden der Organischen Chemie*, vol. XI/1, 1957, pp. 495–506.

Sisido et al., "Synthesis of Racemic Phytophingosine and the *lyxo*Isomer," *Journal of Organic Chemistry*, vol. 34, No. 11, Nov. 1969, pp 3539–3544.

*Chemical Abstracts*, vol. 98, No. 1, Jan. 3, 1983, "Reactions of Esters of Alpha–(Bromoacyl)Acetic Acid with Sodium Thioacetate," p. 4452, Column R, Abstract No.4551u.

*Journal of the Chemical Society*, Perking Transactions 1, No. 2, Feb. 1987, pp. 333–343, Leslie Crombie et al.., "Synthesis of the Mammea Coumarins, Part 2, Experiments in the Mammea E Series and Synthesis of Mammea E/AC".

*Journal of Organic Chemistry*, vol. 43, No. 10, May 12, 1978, pp. 2087–2088, Yuji Oikawa et al., "Meldrum's Acid in Organic Chemistry 2: A General and Versatile Synthesis of Beta–Keto Esters".

C. A. 95:132261 (1981).

*Primary Examiner*—Paul J. Killos
*Attorney, Agent, or Firm*—Finnegan, Henderson, Farabow, Garrett & Dunner, L.L.P.

[57] ABSTRACT

The subject of the invention is a process for the preparation of 2-aminoalkane-1,3,4-triols, in a single stage, preferably a single reduction state, from alkyl 2-hydroxyimino-3-oxo-4-acyloxyalkanoates. The invention makes possible a significant reduction in the number of stages and a marked improvement in the synthesis yields.

29 Claims, No Drawings

PROCESS FOR THE PREPARATION OF 2-AMINOALKANE-1,3,4-TRIOLS

The subject of the invention is a new process for the preparation of ceramide precursors.

Ceramides, in the natural state, are the main components of the lipid layers of the epidermis. They are used in cosmetics, in their natural or synthetic form, in combinations intended, inter alia, to reduce desiccation of the skin or to confer better elasticity on the latter, or alternatively intended for hair treatment.

Natural ceramides are generally obtained by extraction from pigskin, bovine brain, eggs, blood cells or plants (see JP 86/260008 or JP 86120308).

The many disadvantages related to this type of supply (unreliability, contamination, preservation, cost, and the like) meant that the chemical synthesis route was very soon explored.

2-Aminoalkane-1,3,4-triols are known intermediates in the synthesis of certain ceramides; they are, in particular, biological precursors of ceramides 3 and 6. Many synthetic routes have been developed for the preparation of these products. In particular, much work has been carried out on the synthesis of phytosphingosines (see Prostenik, Chem. Phys. Lipids, 1971, 7, 135–143; Isida, J. Org. Chem., 1969, 34, 3539–3544; Jäger, Angew. Chem. Int. Ed. Engl., 1981, 20, 601–605), which belong to the 2-aminoalkane-1,3,4-triol family.

Prostenik provides a 10-stage synthetic route from palmitic acid. This route requires, in particular, 3 different reduction levels and a number of protection and deprotection stages, which results in a very low overall yield.

The route provided by Isida has the same disadvantages. In addition, the starting material that it employs, pentadecanoic acid, is not commercially available.

Finally, Jäger describes a three-stage preparation that uses products known to be toxic (e.g., hexamethylphosphoramide and phenyl isocyanate), under non-industrial conditions, such as a temperature of −78° C., with a difficult purification stage.

This combination of constraints makes these three synthetic routes unusable on an industrial scale, within acceptable cost limits, in the production of the 2-aminoalkane-1,3,4-triols, which are ceramide precursors.

The inventors have therefore sought to improve the synthetic routes to ceramides and, in particular, to their precursors, the 2-aminoalkane-1,3,4-triols.

After lengthy research, the inventors have discovered, surprisingly and unexpectedly, in contrast to what has been constantly taught by the prior art for many years, that the direct synthetic route from an alkyl 2-hydroxyimino-3-oxo-4-acyloxyalkanoate, in a single stage, preferably a reduction stage, can result in a 2-aminoalkane-1,3,4-triol.

By eliminating many stages, the invention makes possible a very substantial saving in time and a much improved synthetic yield, which in industrial terms decreases the cost price of ceramides.

Thus, one subject of the invention is a process for the preparation of 2-aminoalkane-1,3,4-triols, characterized by a conversion, preferably a reduction, in a single stage, of the reducible functional groups of an alkyl 2-hydroxy-imino-3-oxo-4-acyloxyalkanoate of formula (I):

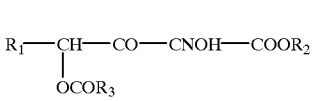

in which $R_1$ represents an alkyl, alkenyl or aralkyl radical, each of which radicals is linear or branched, optionally interrupted by ether bridges, optionally hydroxylated, and optionally a carrier of a $C_1$ to $C_8$ acyloxy functional group, and wherein said alkyl, alkenyl and aralkyl radicals comprise 4 to 28 carbon atoms, $R_2$ represents an alkyl or alkenyl radical, each of which radicals is linear or branched and optionally interrupted by ether bridges, wherein said alkyl radical comprises 1 to 5 carbon atoms and wherein said alkenyl radical comprises 2 to 5 carbon atoms, and $R_3$ represents an alkyl, alkenyl or aryl radical, each of which alkyl and alkenyl radicals is linear or branched, and wherein said alkyl radical comprises 1 to 6 carbon atoms, and wherein said alkenyl radical comprises 2 to 6 carbon atoms, and wherein said aryl radical comprises 3 to 6 carbon atoms, preferably in a solvent and preferably in the presence of at least one hydride.

$R_1$ preferably represents an optionally hydroxylated alkyl radical or alkenyl radical having from 8 to 20 carbon atoms.

According to a preferred embodiment of the invention, $R_2$ is a methyl or ethyl radical.

$R_3$ is preferably chosen from methyl and phenyl radicals.

The process according to the invention makes possible the synthesis, in one stage, of the 2-aminoalkane-1,3,4-triols corresponding to the formula (II):

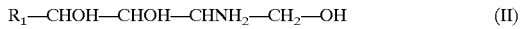

or of the corresponding salts, in which $R_1$ has the same meaning as above.

The compound of formula (II) exists, after synthesis, in the form of a mixture of stereoisomers (enantiomers and/or diastereoisomers).

The solvent is preferably anhydrous. For example, mention may be made, as solvent, of toluene, heptane, tetrahydrofuran, tert-butyl methyl ether or alternatively isopropyl ether. Use is preferably made of tert-butyl methyl ether.

The reaction is preferably carried out under an inert atmosphere, in order to avoid degradation of the reactant by air or water. Nitrogen or argon is generally used for this purpose. The reaction is preferably carried out under an atmosphere composed of argon.

The reaction is preferably initiated at a controlled starting temperature. Controlled starting temperature is understood to mean that the reduction reaction is initiated at a temperature ranging from −10° C. to room temperature. The reaction is preferably initiated at 0° C.

The reaction can be continued at any temperature between −10° C. and the reflux temperature of the solvent used. The reaction is preferably carried out at the reflux temperature of the solvent used.

Mention may be made, among hydrides that preferably can be used according to the invention, of lithium aluminum hydride ($LiAlH_4$) or alternatively sodium bis(2-methoxyethoxy)aluminum hydride (RED-AL™, sold by the company Aldrich, or VITRIDE, sold by the Company Hexcel). Use is more preferably made of sodium bis(2-methoxyethoxy)aluminum hydride.

At the end of the reaction, the product synthesized may be in the form of aluminum complexes. Preferably, in order to restrict the formation of these complexes, minimum amounts of hydride can be used.

Thus, the hydride is generally present in the reaction mixture at a concentration ranging from 3 to 7 molar equivalents with respect to the alkyl 2-hydroxyimino-3-oxo-4-acyloxyalkanoate. Use is preferably made of a concentration ranging from 3 to 6 molar equivalents with respect to the alkyl 2-hydroxyimino-3-oxo-4-acyloxyalkanoate.

At the end of the reaction, marked by the disappearance of the starting materials, the pH of the reaction mixture is preferably brought to a value of less than 2 or greater than 11, by addition to the reaction mixture of acid or base, respectively, which is preferably used in the form of an aqueous solution, in order to destroy the complexes which are possibly formed.

The pH of the reaction mixture is preferably in the region of 1 or in the region of 12. Thus, use is preferably made of hydrochloric acid or of sodium hydroxide respectively.

The alkyl 2-hydroxyimino-3-oxo-4-acyloxyalkanoates corresponding to the formula (I) can be easily prepared by means known to the person skilled in the art. Reference may, for example, be made, for their synthesis, to the document EP-A-0646572, which is incorporated herein by reference.

It is also possible to use, as starting materials, the alkyl 3-oxoalkanoates described in U.S. patent application Ser. No. 08/731,309, filed on Oct. 15, 1996, entitled New Alkyl 3-Oxoalkanoates and Process for the Preparation, in the name of the following inventors Michel Philippe, Bernadette Luppi, Didier Semeria, and Claude Mahieu, which is incorporated herein by reference and a copy of which is attached as Appendix A, and corresponding to the formula (III):

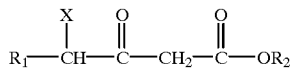

(III)

in which $R_1$ and $R_2$ have the same meaning as above and X denotes a leaving group, as defined by Jerry March in "Advanced Organic Chemistry", Wiley Interscience, 3rd edition, p. 315, Table 10, which is incorporated herein by reference, and X preferably denotes a bromine or chlorine atom or a sulphonate group.

It is possible, for example, to prepare the materials of formula (III) by treating a malonic derivative with an acylating agent. Malonic derivative preferably denotes a monoester or a diester of malonic acid, such as, for example, the isopropylidene ester of malonic acid, also known as Meldrum's acid, or the potassium salt of ethyl malonate. The reaction is preferably carried out in anhydrous medium. It is advantageously carried out in an appropriate solvent such as, for example, tetrahydrofuran, dichloromethane, pyridine or tert-butyl methyl ether.

The alkyl 3-oxoalkanoate compounds corresponding to the formula (III), by nucleophilic substitution, easily result in derivatives corresponding to the formula (IV)

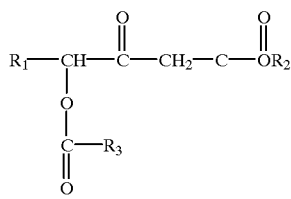

(IV)

in which $R_1$, $R_2$ and $R_3$ have the same definition as above.

The alkyl 3-oxo-4-acyloxyalkanoates according to the formula (IV) then easily result in the alkyl 2-hydroxyimino-3-oxo-4-acyloxyalkanoates according to the formula (I). For example, they can be reacted with an alkyl nitrite in anhydrous medium acidified by gaseous hydrochloric acid. Alkyl nitrite is understood to mean a compound having the formula RONO, in which R represents an alkyl radical having from 2 to 6 carbons, such as, for example, butyl nitrite.

The compound of formula (II) obtained according to the invention can be used in the synthetic processes which can result in ceramides, such as those described by Shapiro, D. (Chemistry of Sphingolipids, Hermann, Paris, 1969, p. 26–34), incorporated by reference herein.

Thus, for example, it is possible to prepare the desired ceramide by acylation of the amine functional group of a 2-aminoalkane-1,3,4-triol by an acid chloride, by an anhydride, by a para-nitrophenol ester, by a succinimide ester, by a dicyclohexylcarbodiimide ester, by a lower alkyl ester or by an azolide, such as, in particular, an imidazolide or a pyrazolide, in anhydrous medium or in a solvent, such as tetrahydrofuran, pyridine, dimethyloformamide or dichloromethane. Advantageously, the anhydride is a mixed anhydride, the lower alkyl ester is a methyl or ethyl ester and the azolide is an imidazolide or a pyrazolide.

Examples of the synthesis according to the invention will now be given, without implied limitation.

EXAMPLES

Example 1

Synthesis of 2-aminooctadecane-1,3,4-triol 0.5 mol of sodium bis(2-methoxyethoxy)-aluminum hydride, as a 70% solution in toluene, was introduced, under argon, with continual stirring, into tert-butyl methyl ether. The solution was then cooled to a temperature of 0° C., and 0.1 mol of methyl 2-hydroxy-imino-3-oxo-4-acetoxyoctadecanoate was slowly added. The reaction mixture was then gradually heated to 50° C. At the end of the reaction, marked by the disappearance of the starting materials, the reaction mixture was hydrolysed while cold with a sodium hydroxide solution. The aqueous phase was separated by settling, and the organic phase was again washed with water and dried, and then the solvent was evaporated under vacuum. After triturating in acetonitrile, a white solid was obtained which, filtered and dried, gave 25 g of 2-amino-octadecane-1,3,4-triol in the form of a white powder.

Yield: 80% Melting point: 132–134° C. $^{13}C$ NMR spectrum ($CDCl_3$): d=14.21, $CH_3$; d=23.09, $CH_3$—$\underline{C}H_2$; d=26.02–26.39 ($C_{12}H_{27}$)—$\underline{C}H_2$—; d=29.8–30.14, $C_3H_7$—$(CH_2)_9$—; d=32.4, $C_2H_5$—$\underline{C}H_2$—; d=33.74–34.29, —$\underline{C}H_2$—CHOH; d=53.11–55.8, CHNH$_2$; d=63.97–65.3, $CH_2OH$; d=71.97–75.88, $\underline{C}H(OH)$—$\underline{C}H(OH)$.

Example 2

Synthesis of the Hydrochloride of 2-amino-octadecane-1,3,4-triol 0.275 mol of lithium aluminum hydride was introduced, under argon, with continual stirring, into tetrahydrofuran.

The solution was then cooled to a temperature of 0° C., and 0.055 mol of methyl 2-hydroxyimino-3-oxo-4-acetoxyoctadecanoate was slowly added. The reaction mixture was then gradually heated to 60° C. At the end of the reaction, marked by the disappearance of the starting materials, the reaction mixture was hydrolysed while cold with a hydrochloric acid solution. A precipitate formed, which was filtered off, and then the solvent was evaporated under vacuum. After crystallizing from a mixture of ethyl ether and acetonitrile, a white solid was obtained which, filtered and dried, gave 14.2 g of 2-aminooctadecane-1,3,4-triol hydrochloride in the form of a white powder.

Yield: 73% The product decomposes beyond 200° C. $^{13}C$ NMR spectrum (CDCl$_3$): d=14.38, CH$_3$; d=23.62, CH$_3$—$\underline{C}$H$_2$; d=26.2–26.75 (C$_{12}$H$_{27}$)—$\underline{C}$H$_2$—; d=30.35–30.79, C$_3$H$_7$—($\underline{C}$H$_2$)$_9$—; d=32.96, C$_2$H$_5$—$\underline{C}$H$_2$—; d=34.37–35.32, —$\underline{C}$H$_2$—CHOH; d=55.14–55–52, CHNH$_2$; d=58.96–61.52, CH$_2$OH; d=70.18–74.18, $\underline{C}$H(OH)—$\underline{C}$H(OH).

We claim:

1. A method for the preparation of a 2-aminoalkane-1,3,4-triol or a salt thereof, comprising the step of converting in a single reduction stage an alkyl 2-hydroxyimino-3-oxo-4-acyloxyalkanoate of formula (I):

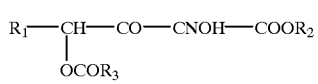

(I)

in which
R$_1$ represents an alkyl, alkenyl or aralkyl radical, each of which radicals is linear or branched, optionally interrupted by ether bridges, optionally hydroxylated, and optionally a carrier of a C$_1$ to C$_8$ acyloxy functional group, and wherein said alkyl, alkenyl, and aralkyl radicals comprise 4 to 28 carbon atoms, R$_2$ represents an alkyl or alkenyl radical, each of which radicals is linear or branched and optionally interrupted by ether bridges, wherein said alkyl radical comprises 1 to 5 carbon atoms and wherein said alkenyl radical comprises 2 to 5 carbon atoms, R$_3$ represents an alkyl, alkenyl or aryl radical, each of which alkyl and alkenyl radicals is linear or branched, and wherein said alkyl radical comprises 1 to 6 carbon atoms, and wherein said alkenyl radical comprises 2 to 6 carbon atoms, and wherein said aryl radical comprises 3 to 6 carbon atoms, to a 2-aminoalkane-1,3,4-triol or a salt thereof.

2. A method according to claim 1, wherein said converting step occurs in at least one solvent.

3. A method according to claim 1, wherein said converting step occurs in the presence of at least one hydride.

4. A method according to claim 2, wherein said converting step occurs in the presence of at least one hydride.

5. A method according to claim 1, wherein as a result of said converting step, said 2-aminoalkane-1,3,4-triol or salt thereof is present in a reaction mixture.

6. A method according to claim 1, wherein R$_1$ is an optionally hydroxylated alkyl or alkenyl radical having from 8 to 20 carbon atoms.

7. A method according to claim 1, wherein R$_2$ is a methyl or ethyl radical.

8. A method according to claim 1, wherein R$_3$ is a methyl or phenyl radical.

9. A method according to claim 2, wherein said solvent is an anyhdrous solvent.

10. A method according to claim 2, wherein said at least one solvent is selected from toluene, heptane, tetrahydrofuran, tert-butyl methyl ether and isopropyl ether.

11. A method according to claim 2, wherein said at least one solvent is tert-butyl methyl ether.

12. A method according to claim 1, wherein said converting step is carried out in an inert atmosphere.

13. A method according to claim 12, wherein said inert atmosphere comprises argon.

14. A method according to claim 3, wherein said at least one hydride is selected from lithium aluminum hydride and sodium bis(2-methoxyethoxy)-aluminimum hydride.

15. A method according to claim 3, wherein said at least one hydride is sodium bis(2-methoxyethoxy)aluminum hydride.

16. A method according to claim 3, wherein said at least one hydride is present in a concentration ranging from 3 to 7 molar equivalents with respect to the alkyl 2-hydroxyimino-3-oxo-4-acyloxyalkanoate.

17. A method according to claim 2, wherein said converting step is initiated at a controlled starting temperature and is then continued at any temperature ranging from –10° C. to the reflux temperature of said solvent.

18. A method according to claim 2, wherein said converting step, once initiated, is continued at the reflux temperature of the solvent.

19. A method according to claim 1, wherein said converting step is initiated at a temperature of 0° C.

20. A method according to claim 5, further comprising, after said converting step, the step of adjusting the pH of said reaction mixture to less than 2 or greater than 11.

21. A method according to claim 20, wherein, after said adjusting step, the pH of said reaction mixture is approximately 1.

22. A method according to claim 20, wherein, after said adjusting step, the pH of said reaction mixture is approximately 12.

23. A method according to claim 20, wherein said reaction mixture is adjusted to a pH of less than 2 using hydrochloric acid.

24. A method according to claim 20, wherein said reaction mixture is adjusted to a pH of greater than 11 using sodium hydroxide.

25. A method for the preparation of a ceramide, comprising:

preparing a 2-aminoalkane-1,3,4-triol or a salt thereof according to the method of claim 1; and acylating the amino functional group of said 2-aminoalkane-1,3,4-triol or a salt thereof to obtain a ceramide.

26. A method according to claim 25, wherein said 2-aminoalkane-1,3,4-triol or salt thereof is acylated by at least one acylating agent selected from an acid chloride, an anhydride, a para-nitrophenol ester, a succinimide ester, a dicyclohexylcarbodiimide ester, a lower alkyl ester and an azolide.

27. A method according to claim 25, wherein said acylating step is performed in an anhydrous medium or in at least one solvent.

28. A method according to claim 27, wherein said at least one solvent is selected from tetrahydrofuran, pyridine, dimethylformamide and dichloromethane.

29. A method according to claim 26, wherein said anhydride is a mixed anhydride, said lower alkyl ester is a methyl or ethyl ester and said azolide is an imidazolide or a pyrazolide.

* * * * *